(12) United States Patent
Mendes et al.

(10) Patent No.: US 6,583,630 B2
(45) Date of Patent: Jun. 24, 2003

(54) SYSTEMS AND METHODS FOR MONITORING WEAR AND/OR DISPLACEMENT OF ARTIFICIAL JOINT MEMBERS, VERTEBRAE, SEGMENTS OF FRACTURED BONES AND DENTAL IMPLANTS

(75) Inventors: Emanuel Mendes, Petah Tikvah (IL); David Mendes, Haifa (IL); Ruth Beer, Haifa (IL); Gilad Barak, Kfar Hanagid (IL)

(73) Assignee: IntelliJoint Systems Ltd., Haifa (IL)

( * ) Notice: Subject to any disclaimer, the term of this patent is extended or adjusted under 35 U.S.C. 154(b) by 0 days.

(21) Appl. No.: 09/774,019

(22) Filed: Jan. 31, 2001

(65) Prior Publication Data

US 2002/0115944 A1 Aug. 22, 2002

(51) Int. Cl.[7] .................................................. G01R 27/28
(52) U.S. Cl. ........................ 324/652; 324/653; 324/639
(58) Field of Search ............................... 324/653, 652, 324/639, 71.2, 240, 242, 649, 633

(56) References Cited

U.S. PATENT DOCUMENTS

| | | | |
|---|---|---|---|
| 4,068,324 A | | 1/1978 | Townley et al. |
| 4,839,593 A | * | 6/1989 | Spies ........................ 324/200 |
| 4,929,896 A | * | 5/1990 | Lara .......................... 324/240 |
| 5,191,286 A | * | 3/1993 | Fischer ...................... 324/230 |
| 5,216,372 A | * | 6/1993 | Zoughi et al. .............. 324/644 |
| 5,420,518 A | * | 5/1995 | Schafer, Jr. ................. 324/653 |
| 5,446,382 A | * | 8/1995 | Flora .......................... 324/232 |
| 5,600,330 A | * | 2/1997 | Blood ......................... 342/463 |
| 5,707,076 A | * | 1/1998 | Takahashi ................... 280/735 |
| 6,025,725 A | * | 2/2000 | Gershenfeld et al. ....... 324/652 |
| 6,288,537 B1 | * | 9/2001 | Vertl et al. .................. 324/230 |
| 6,291,992 B1 | * | 9/2001 | Van Andel et al. ......... 324/240 |

OTHER PUBLICATIONS

Ludwig Bar et al. "SQUID Eddy Current Technique Applying Conformable Eddy Current Probes" ECNDT, 1998, pp. 1–7.*
"QNET Brochure,"WS98 Eddy Current Board, 1998.*
"Honeywell Brochure," Proximity Sensor, No date.*
"Sensorland Brochure," Non–contact Thread Detection, Mar. 2002.*
Guptha, Vilas I., and Neilkirk, Dean, "Design of an Eddy–Current Proximity Sensor using a Two–Coil Planar Transformer" Univ. of Texas, Austin, No date.*

* cited by examiner

Primary Examiner—N. Le
Assistant Examiner—T. R. Sundaram
(74) Attorney, Agent, or Firm—G. E. Ehrlich Ltd.

(57) ABSTRACT

A distance measurement system is provided. The distance measurement system includes at least one resonant circuit, at least one magnetic element with predetermined magnetic properties, a transmitter operable to transmit an electromagnetic pulse, a receiver operable to detect oscillations emitted by said resonant circuit in response to said electromagnetic pulse, and an analyzer operable to analyze an amplitude envelope property of said oscillations, to thereby determine a distance between the resonant circuit and the magnetic element.

51 Claims, 9 Drawing Sheets

SYSTEMS AND METHODS FOR MONITORING WEAR AND/OR DISPLACEMENT OF ARTIFICIAL JOINT MEMBERS, VERTEBRAE, SEGMENTS OF FRACTURED BONES AND DENTAL IMPLANTS

FIELD AND BACKGROUND OF THE INVENTION

The present invention relates to systems and methods for monitoring wear of, and/or displacement between, artificial joint members, vertebrae, segments of fractured bones, and dental implants. More specifically, embodiments of the present invention relate to detection systems capable of determining a distance between, for example, joint members of an artificial joint or between vertebrae, thus enabling to determine, for example, relative displacement therebetween.

Artificial Joints

Total joint arthroplasty is an operation involving the replacement of a damaged joint with an artificial joint assembly in order to restore motion to the joint and function to the muscles and ligaments and other soft tissue structures that operate and control the joint.

The operation is typically performed on individuals with a painful, disabling arthritic joint that is no longer responsive to conservative treatment regimens. This operation typically entails implantation of two or more artificial joint members into respective natural joint members so as to replace deteriorated natural articulating surfaces with artificial equivalents.

Artificial joint assemblies have been devised for a variety of joints including hips, knees, ankles, shoulders, elbows, fingers, toes and wrists. Typically, components of artificial joints such as that shown in, for example, U.S. Pat. No. 4,068,324 to Townley et al. mimic the structure and function of joint members of a natural joint, thus providing as natural as possible articulation motion.

While artificial joint components are designed to provide stable and permanent attachment to the natural adjacent body tissue(s), at attachment interfaces, motion and/or loosening of the artificial joint member can occur, resulting in artificial joint relocation, which can lead to a loss of function, bone deterioration and tissue debris generation.

Such relocation can lead to an increase in wear to the articulating surfaces of the artificial joint. Such wear typically results in reduced function of the artificial joint and, in addition, produces joint debris which are expelled from the joint area to the surrounding tissues and may cause adverse reactions, such as inflammatory granulatoma, in these tissues.

The debris expelled from the artificial joint includes microscopic particles typically measuring up to a few microns in size. These particles provoke various tissue reaction, which affect the bones hosting the artificial joint implant.

The type and severity of the biological reaction to wear generated particles depend mainly on the physical properties and to a lesser degree also on the chemical properties of the wear particles. For example, in joints which include polyethylene component three types of particles are observed, chunks, flakes and granules. The granules, which are approximately one micron in size, are responsible for an intense inflammatory reaction. The histology is characterized by phagocytosis of the particles, resulting in large conglomerations of macrophages due to their inability to digest the polyethylene. The inflammatory process is accompanied by release of biochemical mediators such as prostaglandins and interleukins that cause absorption of the host native bone. Wear particles of other plastics, such as acetyl-copolymer, are of similar physical shapes but may cause an even more intense reaction.

Wear in metallic and ceramic joints is typically characterized by small granules which are taken in by macrophages, leading to a similar biochemical reaction to that caused by plastics.

As a wear of a joint progresses and larger amount of particles are expelled to the surrounding tissues, further bone absorption and loosening of the joint implant may occur. Such loosening of a prosthetic joint implant and damage to surrounding tissues is often left undetected in a patient even if regularly checked by a physician. Most modern methods currently employed for determining the extent of loosening and/or wear of an artificial joint, rely upon either X-ray, computer tomography, isotope bone scan or magnetic resonance to image the implanted joint and are of insufficient accuracy or technically difficult to perform and/or interpret even by highly skilled professionals. In fact, the most modern joint replacement assemblies incorporate metal backed plastic components, metallic components, or ceramic components within metallic shells and as such the available imaging methods cannot produce sufficient contrast in order to determine artificial joint loosening and/or articulating surface wear.

As a result of inefficient detection methods, oftentimes the only indication of early joint loosening is the pain and discomfort suffered by the patient. Oftentimes bone absorption progresses to a stage necessitating replacement surgery using larger implants, and/or bone grafts to accommodate for the lost bone tissue. The prognosis for success and service life of the implant after such a corrective operation is less predictable and depends, among other factors, on the extent of bone absorption suffered. If performed relatively early on, such corrective surgery has an increased chance of success. Therefore, a method capable of detecting the extent and depth of wear of the articulating surfaces of an artificial joint or capable of detecting minute displacement of artificial joint components which are fixed within the bone is of paramount importance both to the patient and the treating physician.

The Spine

The spine is a column of individual vertebrae. Within the spinal column, vertebrae inter-articulate via three joints which form a tripod-like configuration ground the disc occupying the space between the bodies (anteriorly) and the two facet joints (posteriorly).

Degenerative processes of the spine affect all three joints and causes reduction of the disc space in between the vertebrae. Spinal injury may cause instability and loss of bone and may require surgical fusion of the affected vertebrae or vertebral replacement. Fusion is effected by a variety of techniques such as applying bone graft in the damaged disc spaces or by utilizing implanted fixation devices such as screws, cages, plates, rods or hooks.

If fusion is unsuccessful, partial or total lack of union between the vertebrae (non-union) leads to a painful condition which arises from the motion existing between the vertebrae. Such motion, which is oftentimes difficult to detect, often requires additional surgical intervention.

Therefore accurate measurements of implant displacement and of pathological motion during the post operative follow up period as well as subsidence of motion (fusion) is of paramount importance.

Dental Implants

Dental implants are typically composed of a metallic (or other biocompatible material) fixture which is anchored within the maxillary or mandibular bone, a post (e.g., rod or screw) which is attached to the fixture and a prosthetic tooth (typically referred to as a crown, or a cap) which is fitted over the post.

The stability of the implant is essential for longevity thereof and for the preservation of the bone stock. A loose dental implant will cause absorption of bone and further deterioration of the bone stock, often requiring bone reconstruction using various grafting procedures. Thus, it is in the interest of both patient and dental surgeon to detect denial implant loosening prior to bone deterioration.

Bone Fractures

Following traumatic or intentional (osteotomy) bone fractures, natural bone processes unite the fractured or broken bone segments. Oftentimes, the exact time of union remains uncertain and as such, the duration of treatment is oftentimes unnecessarily prolonged.

In addition, when bone segments fail to properly unite, the resulting state of non-union can lead to pain and loss of function in the fractured or broken member.

There is thus a widely recognized need for, and it would be highly advantageous to have, a system and method which enable to monitor relative wear and/or displacement in artificial joints, vertebrae, segments of fractured bones or dental implants thus enabling accurate monitoring of, for example, the state of an implant following an implantation procedure or the state of a bone following a traumatic or intentional fracture.

SUMMARY OF THE INVENTION

According to one aspect of the present invention there is thus provided a distance measurement system, comprising at least one resonant circuit, at least one magnetic element with predetermined magnetic properties, a transmitter operable to transmit an electromagnetic pulse, a receiver operable to detect oscillations emitted by the resonant circuit in response to the electromagnetic pulse, and an analyzer operable to analyze an amplitude envelope property of the oscillations, to thereby determine a distance between the resonant circuit and the magnetic element. In an embodiment, the magnetic element is ferromagnetic. In another embodiment the magnetic element is paramagnetic. In an additional embodiment, the analyzer is operable to determine the amplitude envelope property from an absolute value of amplitudes of the oscillations. In another embodiment the analyzer is operable to determine the amplitude envelope property from relative amplitude values of more than one cycle of the oscillations. In an embodiment the amplitude envelope property is an amplitude rate of decay. In an additional embodiment the analyzer is operable to determine the distance between the resonant circuit and the magnetic element additionally from frequency properties of the oscillations.

In a preferred embodiment the distance measurement system comprises more than one resonant circuit, to thereby determine more than one distance between the resonant circuits and the at least one magnetic element. Another embodiment is operable to determine the distance between the resonant circuits and the at least one magnetic element in more than one dimension. In another embodiment the more than one resonant circuits are operable to resonate at different frequencies.

Another embodiment comprises more than one magnetic element, to thereby determine more than one distance between the at least one resonant circuit and the magnetic elements. Another embodiment preferably, is operable to determine the distance between the at least one resonant circuit and the magnetic elements in more than one dimension.

Another embodiment comprises more than one resonant circuit and more than one magnetic element, to thereby determine more than one distance between the resonant circuits and the magnetic elements. Another embodiment preferably is operable to determine the distance between the resonant circuits and the at least one magnetic element in more than one dimension.

In a preferred embodiment the analyzer comprises a look-up table, comprising relationships between measured oscillations end distances. In another embodiment the relationships are per-system relationships. In an additional embodiment, the relationships comprise in-situ calibrations.

According to another aspect of the present invention there is thus provided a method for assembling a distance measurement system, comprising the steps of: placing a resonant circuit at a first location, placing a magnetic element with predetermined magnetic properties at a second location, providing a transmitter for transmitting an electromagnetic pulse to the resonant circuit, providing a detector for detecting oscillations emitted by the resonant circuit in response to the electromagnetic pulse, and providing oscillations, to thereby determine a distance between the first location and the second location. In an embodiment, the analyzer comprises a look-up table of relationships between measured oscillations and distances, and wherein the look-up table values are established for each one of a predetermined set of distances by performing for each predetermined distance the steps of transmitting an electromagnetic pulse to the resonant circuit, detecting oscillations emitted by the resonant circuit in response to the electromagnetic pulse, and measuring an amplitude envelope property of the detected oscillations, to thereby establish a look-up table value for the distance.

According to yet another aspect of the present invention there is thus provided a method for measuring the distance between a first location comprising a resonant circuit and a second location comprising a magnetic element, comprising the steps of transmitting an electromagnetic pulse to the resonant circuit, detecting oscillations emitted by the resonant circuit in response to the electromagnetic pulse, and analyzing an amplitude envelope property of the detected oscillations, to thereby determine a distance between the first location and the second location. In a preferred embodiment, the step of analyzing an amplitude envelope property further comprises comparing information detected from the emitted oscillations to information in a look-up table, of relationships between measured oscillations and distances. Another embodiment comprises obtaining the amplitude envelope property from an absolute value of amplitudes of the oscillations. Another preferred embodiment comprises obtaining the amplitude envelope property from relative amplitude values of more than one cycle of the oscillations. Another embodiment, comprises making use of an amplitude rate of decay as the amplitude envelope property. Another embodiment comprises additionally detecting the distance from frequency properties of the detected oscillations.

According to still another aspect of the present invention there is thus provided a distance measurement system utilizing eddy currents for energy dissipation, the system comprising: at least one resonant circuit, at least one magnetic element with predetermined magnetic properties, a transmitter operable to transmit an electromagnetic pulse, a receiver operable to detect oscillations emitted by the resonant circuit in response to the electromagnetic pulse, and an analyzer operable to analyze an amplitude envelope property of the oscillations as an indicator of eddy current induced energy dissipation, to thereby determine a distance between the resonant circuit and the magnetic element.

According to yet an additional aspect of the present invention there is thus provided an artificial joint system comprising: (a) at least one artificial joint member having an articulating surface and a bone attachment portion, the bone attachment portion being for attaching the at least one artificial joint member to at least one natural bone of a joint when implanted within an individual; (b) a detection system implanted within, or attached to, the at least one artificial joint member and the at least one natural bone of the joint the at least one detection system including: (i) at least one resonant circuit element; and (ii) at least one magnetic element having predetermined magnetic properties; and (c) an extracorporeal unit including; (i) a transmitter operable to transmit an electromagnetic pulse; (ii) a receiver operable to detect oscillations emitted by the resonant circuit in response to the electromagnetic pulse; and (iii) an analyzer operable to analyze all amplitude envelope property of the oscillations, the amplitude envelope property being indicative of a distance between the resonant circuit and the magnetic element and thus of a distance between the at least one artificial joint member and the at least one natural bone of the joint.

According to still another aspect of the present invention there is thus provided, a method of determining a parameter associated with relative displacement between an artificial joint member and a natural bone of a joint to which it is attached, the method comprising: (a) providing a detection system implanted within, or attached to, at least one artificial joint member and at least one natural bone of a joint, the detection system including: (i) at least one resonant circuit element; and (ii) at least one magnetic element having predetermined magnetic properties; (b) extracorporeally energizing the detection system so as to receive outside the body an information signal including oscillations emitted by the resonant circuit in response to the energizing; and (c) processing the information signal being received so as to yield an amplitude envelope property of the oscillations, the amplitude envelope being indicative of a distance between the resonant circuit and the magnetic element, and thus of a distance between the at least one artificial joint member and the at least one natural bone of the joint.

According to yet an additional aspect of the present invention there is thus provided an artificial joint system comprising: (a) an artificial joint assembly implantable within an individual, the artificial joint assembly including a first artificial joint assembly member having a first articulating surface and further including a second artificial joint assembly member having a second articulating surface, the first and the second articulating surfaces being in articulating engagement therebetween; (b) a detection system implanted within or attached to, the artificial joint assembly, the detection system including: (i) at least one resonant circuit element; and (ii) at least one magnetic element having predetermined magnetic properties; and (c) an extracorporeal unit including: (i) a transmitter operable to transmit an electromagnetic pulse, (ii) a receiver operable to detect oscillations emitted by the resonant circuit in response to the electromagnetic pulse; and (iii) an analyzer operable to analyze an amplitude envelope property of the oscillations, the amplitude envelope property being indicative of a distance between the resonant circuit and the magnetic element and thus of a distance between the first artificial joint assembly member and the second artificial joint assembly member.

According to still an additional aspect of the present invention there is thus provided a method, of determining a parameter associated with wear or relative displacement of an artificial joint, the method comprising the steps of, (a) providing an artificial joint assembly system including: (i) an artificial joint assembly implantable within an individual, the artificial joint assembly including a first artificial joint assembly member having a first articulating surface and further including a second artificial joint assembly member having a second articulating surface, the first and the second articulating surfaces being in articulating engagement therebetween; and (ii) a detection system implanted within, or attached to, the artificial joint assembly, the detection system including at least one resonant circuit element; and at least one magnetic element having predetermined magnetic properties; (b) extracorporeally energizing the detection system so as to receive outside the body an information signal including oscillations emitted by the resonant circuit in response to the energizing; and (c) processing the information signal being received so as to yield an amplitude envelope property of the oscillations, the amplitude envelope being indicative of a distance between the resonant circuit and the magnetic element, and thus of a distance between the first artificial joint assembly member and the second artificial joint assembly member.

In a preferred embodiment the at least one artificial joint member includes al least two artificial joint members, each attached to a specific natural bone of the joint of the at least one natural bone of the joint, whereas the articulating surfaces of the at least two artificial joint members are configured to allow articulating engagement therebetween.

In a preferred embodiment the at least one resonance circuit element includes a plurality of distinct resonance circuit elements each producing a distinct signal of oscillating frequency upon reception of the electromagnetic pulse, the distinct signal being a function of a distance between a specific resonance circuit element of the plurality of distinct resonance circuit elements and the at least one magnetic element.

In a preferred embodiment the at least one artificial joint member forms a part of an artificial joint selected from the group consisting of an artificial shoulder joint, an artificial hip joint, an artificial knee joint, an artificial elbow joint, an artificial ankle joint, an artificial wrist joint, an artificial carpo-metacarpal joint, an artificial metacarpo-phalangeal joint, an artificial interphalangeal joint and an artificial metatarso-phalangeal joint.

In a preferred embodiment the at least one artificial joint member is fabricated from at least one material selected from the group consisting of stainless steel, titanium alloy, cobalt alloy, polyethylene or other polymers, ceramics and composites materials.

In a preferred embodiment the at least one resonance circuit element is implanted within, or attached to, the bone attachment portion of the at least one artificial joint member, and further wherein the at least one magnetic element is implanted within, attached to, or forms a part of the bone attachment portion of the at least one artificial joint member.

In a preferred embodiment the first and the second artificial joint assembly members each include a portion distant to the articulating surface thereof, the portion being for attaching each of the first and the second artificial joint assembly members to a natural bone of a joint when implanted within the individual, According to a further aspect of the present invention there is thus provided a system for monitoring displacement between vertebrae comprising: (a) a detection system implanted within, or attached to, the vertebrae, the detection system including: (i) at least one resonant circuit element; and (ii) at least one magnetic element having predetermined magnetic properties; (b) an extracorporeal unit including: (i) a transmitter operable to transmit an electromagnetic pulse; and (ii) a receiver operable to detect oscillations emitted by the resonant circuit in response to the electromagnetic pulse; and (iii) an analyzer operable to analyze an amplitude envelope property of the oscillations, the amplitude envelope property being indicative of a distance between the resonant circuit and the magnetic element and thus of a distance between the vertebrae.

According to still a further aspect of the present invention there is thus provided a method of determining a parameter associated with relative displacement of vertebrae, the method comprising the steps of: (a) attaching or implanting a detection system within or upon the vertebrae, the detection system including: (i) at least one resonant circuit element; and (ii) at least one magnetic element having predetermined magnetic properties; (b) extracorporeally energizing the detection system so as to receive outside the body an information signal including oscillations emitted by the resonant circuit in response to the energizing; and (c) processing the information signal being received so as to yield an amplitude envelope property of the oscillations, the amplitude envelope being indicative of a distance between the resonant circuit and the magnetic element, and thus of a distance between the vertebrae, In a preferred embodiment at least one of the vertebrae is an artificial vertebra. According to yet a further aspect of the present invention there is provided According to yet a further aspect of the present invention there is thus provided a system for monitoring displacement between a dental implant and a bone in which it is anchored comprising: (a) a detection system implanted within, or attached to, the dental implant and the bone, the detection system, including: (i) at least one resonant circuit element; and (ii) at least one magnetic element having predetermined magnetic properties; and (b) an extracorporeal unit including: (i) a transmitter operable to transmit an electromagnetic pulse: (ii) a receiver operable to detect oscillations emitted by the resonant circuit in response to the electromagnetic pulse; and (iii) an analyzer operable to analyze an amplitude envelope property of the oscillations, the amplitude envelope property being indicative of a distance between the resonant circuit and the magnetic element and thus of a distance between the dental implant and the bone.

According to still a further aspect of the present invention there is thus provided a method of determining a parameter associated with relative displacement between a dental implant and a bone in which it is anchored, the method comprising the steps of: (a) providing a detection system within the dental implant and the bone, the detection system including: (i) at least one resonant circuit element; and (ii) at least one magnetic element having predetermined magnetic properties; (b) extracorporeally energizing the detection system so as to receive outside the body an information signal including oscillations emitted by the resonant circuit in response to the energizing, and (c) processing the information signal being received so as to yield an amplitude envelope property of the oscillations, the amplitude envelope being indicative of a distance between the resonant circuit and the magnetic element and thus of a distance between, the dental implant and the bone.

According to still a further aspect of the present invention there is thus provided a system for monitoring displacement between bone segments of a fractured or a broken bone comprising: (a) a detection system implanted within, or attached to, the bone segments, the detection system including: (i) at least one resonant circuit element; and (ii) at least one magnetic element having predetermined magnetic properties; and (b) an extracorporeal unit including: (i) a transmitter operable to transmit an electromagnetic pulse; (ii) a receiver operable to detect oscillations emitted by the resonant circuit in response to the electromagnetic pulse and (iii) an analyzer operable to analyze an amplitude envelope property of the oscillations, the amplitude envelope property being indicative of a distance between the resonant circuit and the magnetic element and thus of a distance between the bone segments of the fractured or broken bone.

In a preferred embodiment the system further comprising at least one anchor element being for attaching the detection system to the bone segments.

In a preferred embodiment the at least one anchor element forms a part of an implant.

In a preferred embodiment the implant serves for interfixating the bone segments.

According to still a further aspect of the present invention there is thus provided a method of determining a parameter associated with relative displacement between bone segments of a fractured or broken bone, the method comprising the steps of (a) attaching or implanting a detection system within or upon the bone segments, the detection system including: (i) at least one resonant circuit element; and (ii) at least one magnetic element having predetermined magnetic properties; (b) extracorporeally energizing the detection system so as to receive outside the body an information signal including oscillations emitted by the resonant circuit in response to the energizing; and (c) processing the information signal being received so as to yield an amplitude envelope property of the oscillations, the amplitude envelope being indicative of a distance between the resonant circuit and the magnetic element, and thus of a distance between the bone segments of the fractured or broken bone.

The present invention successfully addresses the shortcomings of the presently known configurations by providing systems and methods with which a wear and/or displacement of members of an implanted artificial joint assembly, or displacement of bone segments, vertebrae or dental implants can be determined in an easy and accurate manner.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description, taken with the drawings making apparent to those skilled in the art how the several forms of the invention may be embodied in practice.

In the drawings.

DESCRIPTION OF THE PREFERRED EMBODIMENTS

Figure 1:
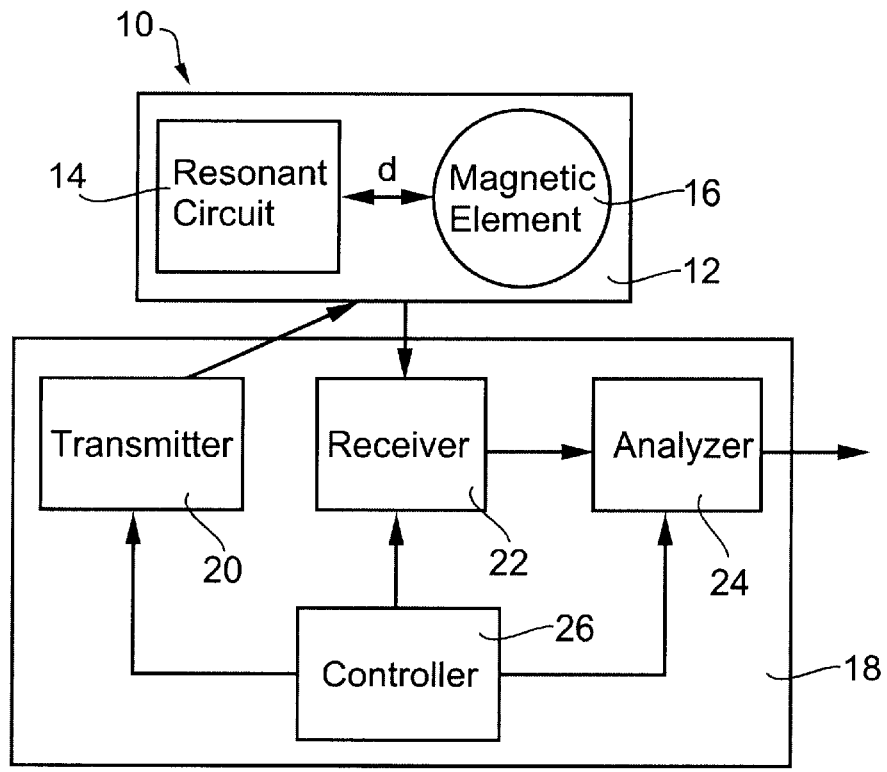
FIG. 1 is a simplified block diagram of a preferred embodiment of a distance measurement system of the present invention.

The present invention is of systems and methods which can be utilized to monitor relative displacement between artificial joint members, bone segments and vertebrae. Specifically, the present invention can be used to monitor a distance between, for example, artificial joint members by monitoring a distance-dependent effect of a magnetic element implanted within one artificial joint member on an amplitude of a signal emitted from a resonant circuit which is implanted, within a second artificial joint member.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have discovered that a decaying effect of eddy currents produced in a magnetic element on an amplitude of an oscillating signal generated from a resonant circuit is proportionally related to a distance separating the magnetic element and the resonant circuit and that such a distance-effect relationship can be calibrated, The following is a detailed description of the principles governing the above described relationship and of novel systems and methods which employ sensors which rely on such principles for determining or monitoring a distance between two or more objects.

When a resonant circuit is energized by a short pulse, the circuit begins to oscillate at the free resonant frequency. The free oscillation frequency of a resonant circuit is represented by:

$$f=0.5*\pi*(L*C)^{0.5}$$

If no additional external energy is provided, the amplitude of the oscillation with decay. The amplitude rate of decay, absolute amplitude, and exact resonance frequency are influenced by two main factors. The first factor is the internal equivalent resistance of the circuit due to circuit elements. The second factor is the external equivalent resistance due to eddy currents at elements that interfere with the magnetic field of the resonant circuit. Magnetic elements placed in proximity to the resonant circuit create such interference, and influence the resonant circuit response to the energizing pulse. The characteristics of the oscillation induced in the resonant circuit by the energizing pulse may be used to measure the distance between a resonant circuit and a magnetic element. This physical principle is the basis for the distance measurement system of the present invention.

Reference is now made to FIG. 1, which is a simplified block diagram of a preferred embodiment of a distance measurement system, which is referred to hereinunder as system 10.

System 10 includes two subsystems, a sensor subsystem 12 and an analysis subsystem 18. The sensor subsystem 12 includes at least one resonant circuit 14 and at least one magnetic element 16, separated by a distance d, which can be determined by system 10 as is further described below.

Analysis subsystem 18 includes a transmitter 20, receiver 22, and analyzer 24, all of which are controlled by controller 26.

Transmitter 20 serves for transmitting a short electromagnetic pulse which energizes the resonant circuit 14 when impinging thereupon. In response to this short electromagnetic pulse, sensor subsystem 12 emits a damped oscillation, which is received by receiver 22. The characteristics of the emitted signal depend upon the properties of resonant circuit 14 and magnetic element 16, and upon the distance d between them. The received signal is analyzed by analyzer 24, which analyzes the received signal characteristics to thereby determine distance d, as will be described in detail below. Controller 26 controls and coordinates all analysis subsystem 18 functions.

Figure 2:
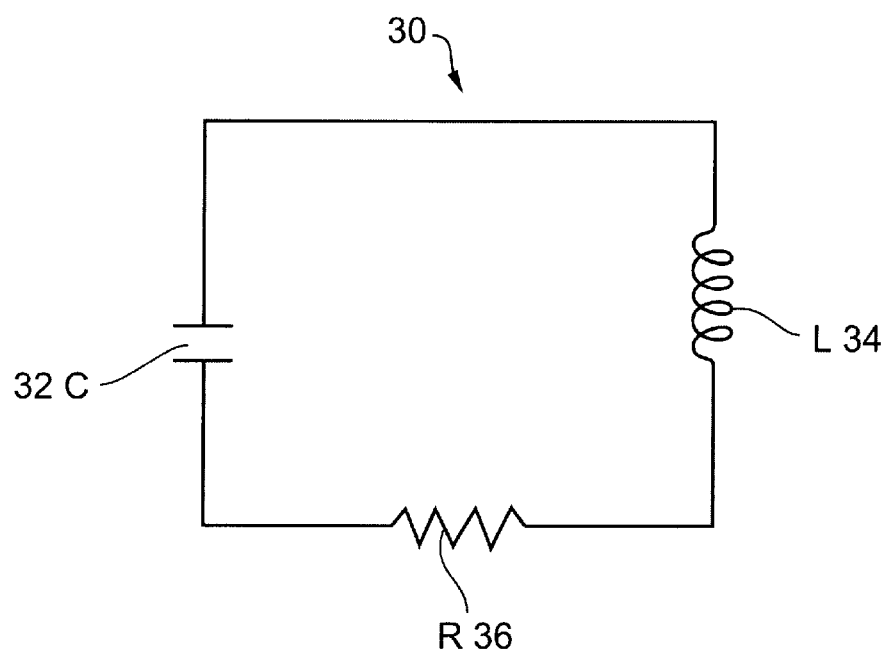
FIG. 2 is a simplified diagram of a resonant circuit utilizable by the system of the present invention.

Reference is now made to FIG. 2, which is a simplified diagram of a preferred embodiment of a resonant circuit 30. Resonant circuit 30 is a simple RLC circuit including a capacitor (C) 32, an inductor (L) 34, and a resistor (R) 36. The resonant frequency of resonant circuit 30 depends primarily on the values of capacitor 32 and inductor 34, as defined in the above equation. The value of resistor 36, along with other dissipative effects produced by, for example, eddy currents in elements which interfere with the circuit's magnetic field, determines the circuit's amplitude rate of decay, as discussed above.

Figure 3:
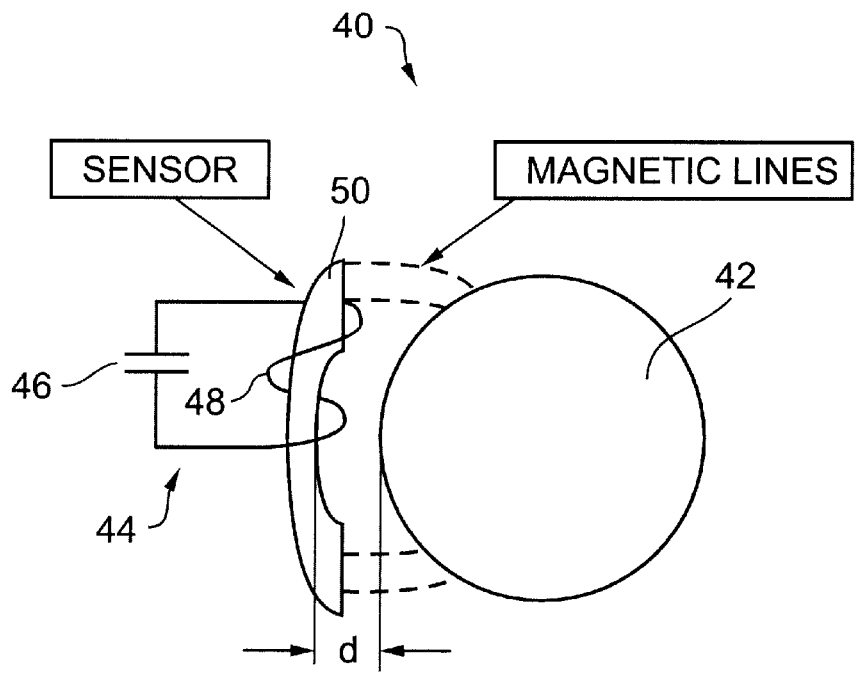
FIG. 3 is a simplified diagram of a sensor subsystem according to the teachings of the present invention.

Reference is now made to FIG. 3, which is a simplified diagram of a preferred embodiment of a sensor subsystem 40. Magnetic element 42 includes a material having magnetic properties such as, for example, a ferromagnetic material or a paramagnetic material.

Resonant circuit 44 includes a capacitor 46 and a coil 48 wound on a core 50. When resonant circuit 44 is energized by an electromagnetic pulse, the circuit emits a damped oscillatory electromagnetic signal. The characteristics of the emitted signal may be affected by the distance between magnetic element 42 and resonant circuit 44.

Figure 4:
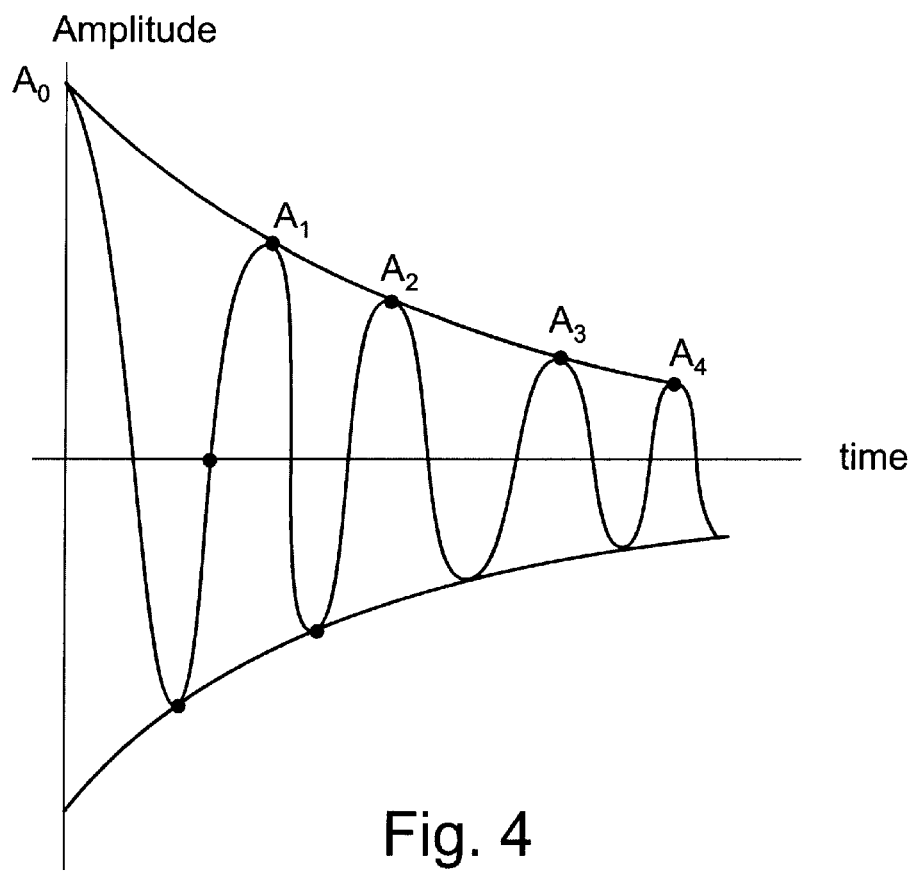
FIG. 4 illustrates an example of damped oscillation.

Reference is now made to FIG. 4. which exemplifies damped oscillation. The oscillation shown has two main characteristics. The first characteristic is the rate at which the amplitude of the oscillation decreases over time. The second characteristic is the frequency of the oscillation.

As shown in FIG. 4, the amplitude of the generated damped oscillations may be represented by a decreasing series of values, $A_0$ to $A_n$. The amplitude of the initial oscillation is $A_0$ and the amplitude of the $n^{th}$ oscillation is $A_n$, where n equals four in FIG. 4. The amplitude of the damped oscillations is a function of the energy absorbed at each cycle by the internal equivalent resistance of the resonant circuit 44, and by the external equivalent resistance due to eddy currents at elements, such as magnetic element 42, which interfere with the magnetic field of resonant circuit 44. The amount of interference generated by magnetic element 42 is a function of the distance d between magnetic element 42 and resonant circuit 44.

As such, amplitudes, $A_i$, of the oscillations produced by sensor subsystem 40 can be used to determine distance d. For example, distance d an be determined from the absolute value of the amplitudes of one or more cycles of oscillation produced by sensor subsystem 40.

Any reference to amplitude values in this or later embodiments may be to peak-to-peak amplitude, negative peak amplitude, positive peak amplitude, or any other amplitude indicator.

Figure 5:
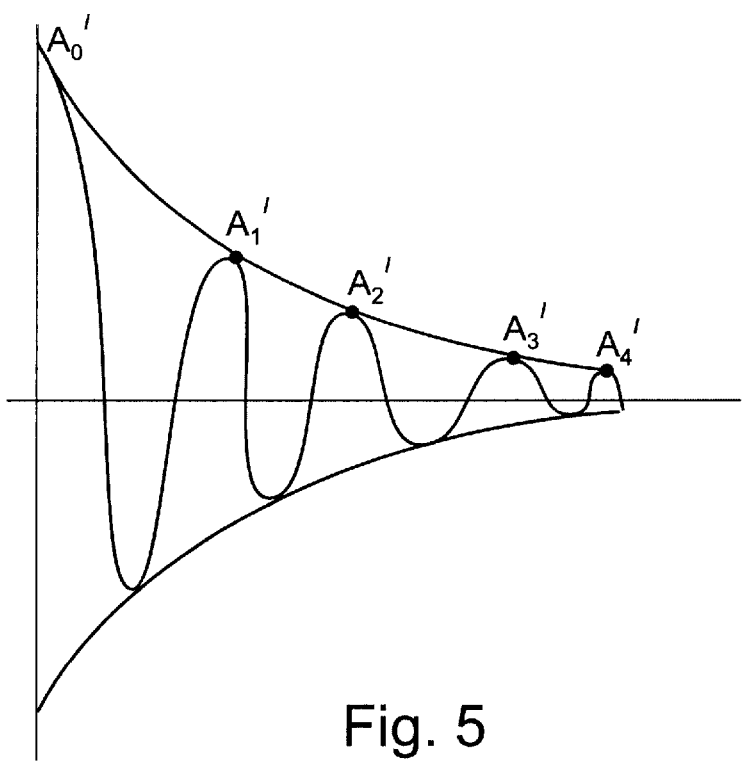
FIG. 5 illustrates another example of damped oscillation.

Reference is now made to FIG. 5, which illustrates a second example of damped oscillation. The absolute amplitudes of the oscillations $A_i'$ differ from the absolute amplitudes $A_i$ in FIG. 4. Changing the distance d between resonant circuit 30 and the magnetic element 42 affects the absolute signal amplitudes. Distance d may be detected by analyzing the absolute amplitudes of the emissions received from the sensor subsystem 40.

In a second preferred embodiment, the distance d is measured by analyzing the relative values of the amplitudes of successive cycles of emissions received from the sensor subsystem 40. In the preferred embodiment, the relative amplitudes are compared by examining the ratios:

$$A_r(ik)=A_i/A_{i+k}$$

where $A_i$ is the amplitude of the i-th oscillation, and $A_{i+k}$ is the amplitude after k subsequent oscillations. Higher resolution may be obtained by increasing k, however k is preferably not increased to the point where noise effects compromise amplitude measurements.

In addition to measuring amplitudes, $A_i$, of the oscillations produced by sensor subsystem 40, system 10 of the present invention can also provide a user with information pertaining to an effect of distance d on an oscillation frequency of a signal produced by resonant circuit 44. Such information can be used along with amplitude measurement information to provide highly accurate distance measurements.

Distance d may change the oscillation frequency due to the proximity of the magnetic element 42 to the resonant circuit 44. The oscillation frequency of resonant circuit 44 is determined primarily by the values of the capacitor 46 and the coil 48. However the distance of magnetic element 42 from resonant circuit 44 also influences the values of the reactive elements of the circuit. The values of the reactive elements, and hence the emitted frequency, depend upon both the magnetic characteristics of the magnetic element 42, and its distance from the resonant circuit 44 if the magnetic properties of magnetic element 42 are known, the emitted frequency may be used as an additional indicator of the distance d.

Figure 6:
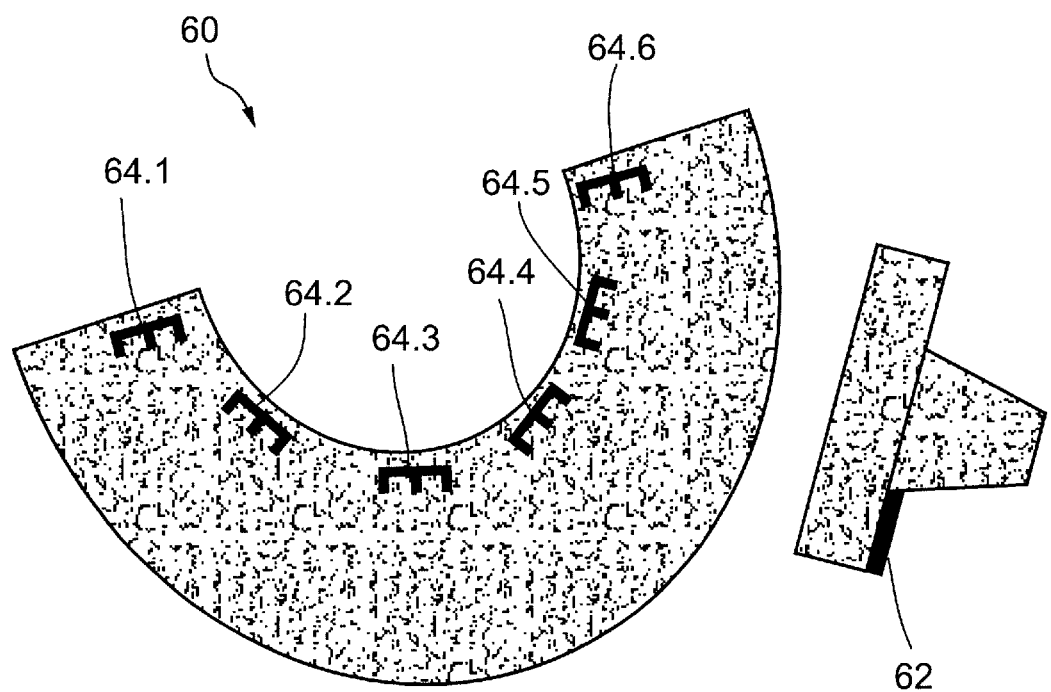
FIG. 6 is a simplified sensor subsystem having more than one resonant circuit according to the teachings of the present invention.

Reference is now made to FIG. 6, which illustrates a sensor subsystem 60 which includes more than one resonant circuit. Subsystem 60 includes one magnetic element 62 and several resonant circuits 64.1 . . . 64.6, In a preferred embodiment, each resonant circuit is tuned to a different frequency. The number of resonant circuits may vary over different configurations. Each resonant circuit 64,i is located at a distance $d_i$ from magnetic element 62. Each resonant circuit emits a damped oscillation in response to a transmitted electromagnetic pulse. The total emission from the sensor subsystem 60 depends upon distances $d_i$.

Distances $d_i$ may be measured simultaneously by analyzing the sensor subsystem emissions.

Preferably, resonant circuits 64 are designed, to emit at different free oscillation frequencies in order to distinguish the signal emitted by each resonant circuit 64. If the free oscillation frequencies are adequately separated and the resonant circuits tuned accordingly, the emission parameters of each resonant circuit may be easily distinguished.

In another preferred embodiment, the subsystem 60 includes more than one magnetic element. Each magnetic element i is located at a distance $d_i$ from the resonant circuit. The resonant circuit emits a damped oscillation in response to the transmitted electromagnetic pulse. The characteristics of the sensor subsystem emission depend upon the distances $d_i$. The distances $d_i$ may be measured simultaneously by analyzing the total emission output from the sensor subsystem.

In another embodiment the sensor subsystem includes more than one magnetic element and more than one resonant circuit. Each magnetic element i is located at a distance $d_{ik}$ from resonant circuit k. The resonant circuits emit damped oscillations in response to the transmitted electromagnetic pulse. The characteristics of the total emission from the sensor subsystem depend upon the distances $d_{ik}$. Distances $d_{ik}$ may be measured simultaneously by analyzing the total emission output from the sensor subsystem, In a preferred embodiment of the present invention, a dedicated look-up table is used to enable analysis of the emitted signal, and to eliminate variations due to production tolerances. The look-up table stores information about emitted signal characteristics at several distances. Intermediate distances may be calculated by interpolation. The look-up table may be used to compensate for non-linearities in the resonant circuit response as a function of distance from the magnetic element. In the preferred embodiment the signal characteristic stored in the look-up table is the value of a preselected amplitude ratio, for example $A_0/A_{20}$. In one preferred embodiment the values stored in the look-up are expected signal characteristics. In another preferred embodiment, the values stored in the look-up table are specific to each device. These values are determined by testing each device following fabrication, In another embodiments the distance d is determined, by linear interpolation of the amplitude.

Figure 7:
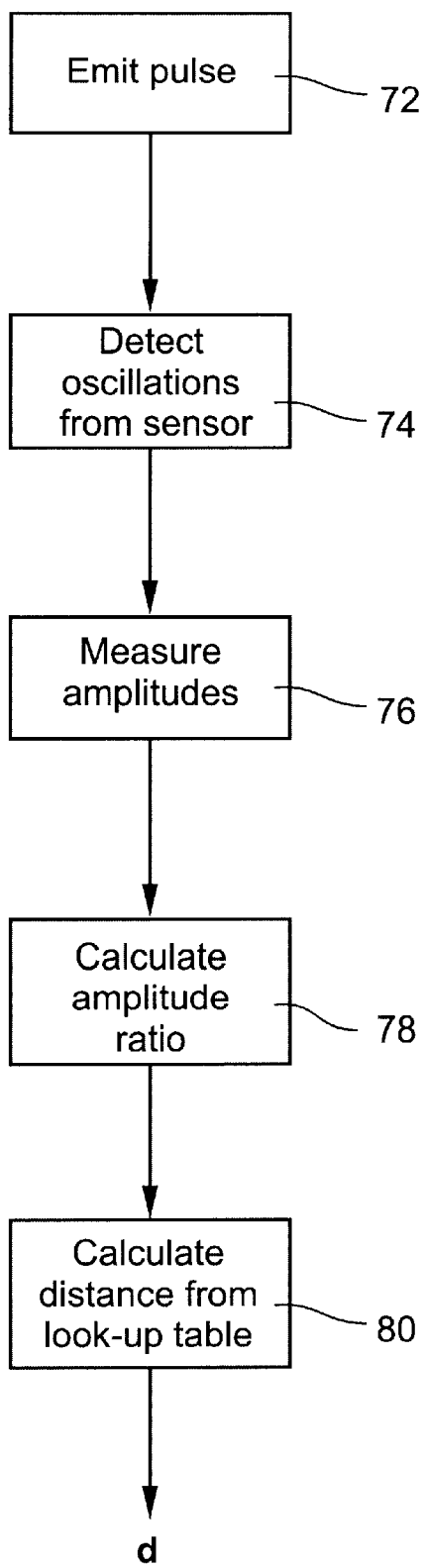
FIG. 7 is a simplified flow chart illustrating a distance measurement process according to the teachings of the present invention.

Reference is now made to FIG. 7, which is a simplified flow chart illustrating one possible distance measurement process of system 10.

Measurement is initiated by generating an electromagnetic pulse in the vicinity of the sensor subsystem, as indicated by step 72. As a response, the sensor subsystem emits a damped oscillation, as indicated by in step 74. The amplitudes of the required cycles of the detected oscillation are measured, as indicated by step 76. The measured amplitudes are divided to thereby form an amplitude ratio, as indicated by step 78. Finally, a look-up table is used to convert he calculated ratio into a distance measurement, as indicated by step 80.

The embodiments of distance measurement systems described above all utilize the effect of eddy currents on resonant circuit emissions to measure the distance between one or more resonant circuits and one or more magnetic elements. Various signal parameters, such as absolute amplitude, relative amplitude, and frequency may be utilized to determine the distance between each resonant circuit and each magnetic element.

System 10 of the present invention can be used for determining a distance or for monitoring a change in a distance between any objects which are placed several millimeters to several meters apart while providing highly accurate distance measurements with a resolution of several microns or less. The effectiveness of system 10 at various distance ranges depends mainly on the size and configuration of the sensor subsystem elements employed.

Such a high degree of accuracy makes system 10 of the present invention ideal for measuring tolerances in various fabrication processes.

As is further described below, system 10 of the present invention is particularly useful for measuring distances and/or monitoring a change in a distance between body implanted elements, such as for example, artificial joint members, vertebrae, bone segments and the like.

Thus, according to another aspect of the present invention there is provided an artificial joint system, which is referred to herein as system 100.

Figure 8:
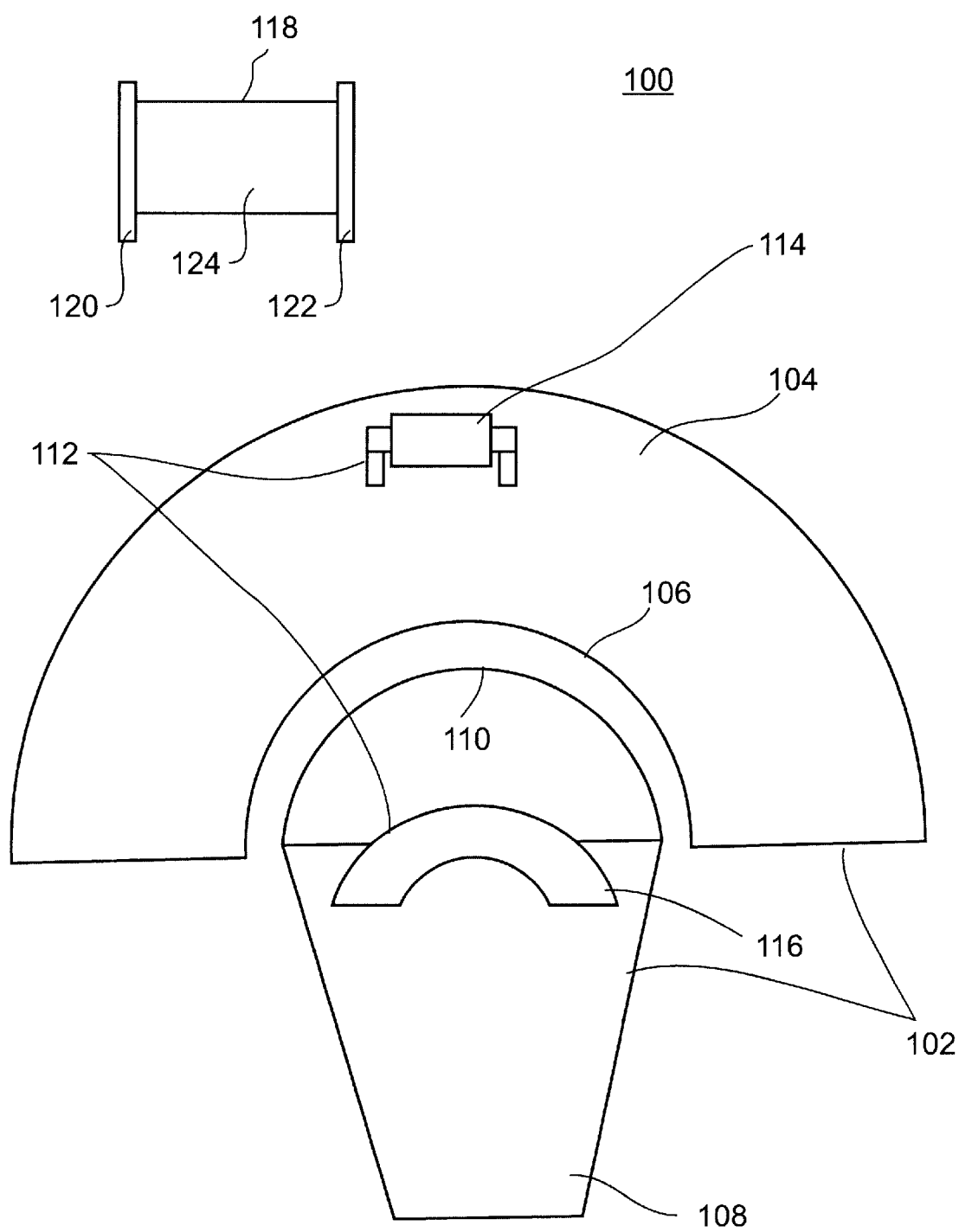
FIG. 8 illustrates an artificial joint system for monitoring displacement between artificial joint members according to the teachings of the present invention.

As shown in FIG. 8, system 100 includes an artificial joint assembly 102 which is implantable within an individual. Artificial joint assembly can be, for example, an artificial shoulder joint assembly, an artificial hip joint assembly, an artificial elbow joint assembly, an artificial ankle joint assembly, an artificial wrist joint assembly, an artificial carpo-metacarpal joint assembly, an artificial metacarpo-phalangeal joint assembly, an artificial interphalangeal joint assembly, an artificial knee joint assembly or an artificial metatarso-phalangeal joint assembly.

In the example given in FIG. 8, artificial Joint assembly 102 includes a first artificial joint assembly member 104 having a first articulating surface 106 and a second artificial joint assembly member 108 having a second articulating surface 110. Articulating surfaces 106 and 110 are in articulating engagement therebetween when assembly 102 is implanted within the body.

System 100 further includes a detection system 112 which is implanted within, or attached to, artificial joint assembly 102.

Detection system 112 is similar in function to sensor subsystem 12 described above. Thus, detection system 112 includes at least one resonant circuit 114 and at least one magnetic element 116 which function in a similar fashion to the components of sensor subsystem 12 described hereinabove.

System 100 further includes an extracorporeal unit 118 which is similar to analysis subsystem 18 described above As such, extracorporeal unit 118 includes a transmitter 120, receiver 122, and analyzer 124, all of which are controlled by controller 126. Transmitter 120 serves for generating an interrogation signal (e.g., electromagnetic pulse) from outside of the body, which signal energizes detection system 112 placed within the body. The energized resonance circuit of detection system 112 produces the oscillating signal described hereinabove which is received outside the body by receiver 122 of extracorporeal unit 118.

Analyzer 124 processes the received signal to determine a distance between resonant circuit 114 and magnetic element 116 as described hereinabove with reference to components of system 10. Periodic determination of such a distance over a predetermined time period, enables a user to determine relative wear of articulating surfaces 106 and 110.

Detection system 112 and extracorporeal unit 118 described above can also be utilized to measure a distance between at least one artificial joint member and at least one natural bone of a joint into which the at least one artificial joint member is implanted.

Figure 9:
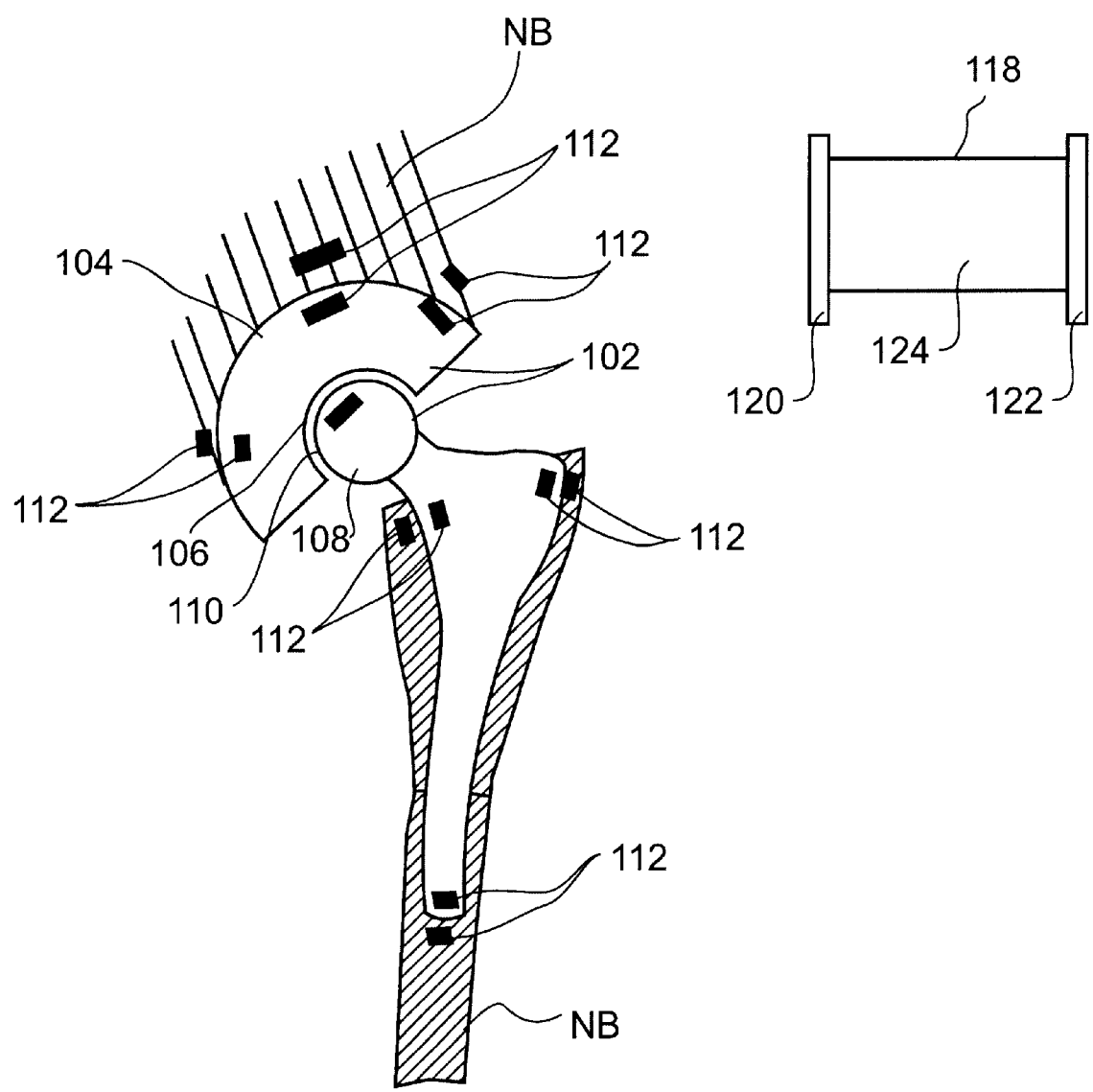
FIG. 9 illustrates an artificial joint system for monitoring displacement between an artificial joint member and a bore into which it implanted according to the teachings of the present invention.

As illustrated in FIG. 9, detection system 112 can be implanted within a natural bone (NB) of a joint 136 and an artificial joint member 130 having an articulating surface 132 and a bone attachment portion 134.

In such a case, use of extracorporeal unit 118 enables to periodically determine a distance between resonant circuit 114 and magnetic element thus enabling determination of relative displacement between artificial joint member 130 and natural bone 136. This enables a user to detect extremely small changes in a distance between artificial joint member (s) and reference points in bone(s) which changes can be caused by, for example, artificial joint loosening and/or bone deterioration.

Thus, detection system 112 and extracorporeal unit 118 of the present invention enable accurate and simple monitoring of a state of an artificial joint implanted in an individual. The information providable thereby enables a treating physician to detect early on, bone deterioration and implant loosening and/or any articulating surface wear which may lead to the development of bone absorption and/or loosening of the joint implant. Early detection of displacement and/or wear enables the physician to determine a most suitable course of treatment if necessary. In addition detection system 112 and extracorporeal unit 118 of the present invention allow a physician, to detect displacements of joint members which can be at times left unnoticed by the patient or treating physician but which may progress into severe joint damage.

Detection system 112 and extracorporeal unit 118 of the present invention can also be utilized to monitor displacement between fixed or inter-articulating body constituents, either natural and/or implanted.

For example, detection system 112 and extracorporeal unit 118 can be designed and configured for monitoring displacement between vertebrae, including any combination of artificial and/or natural vertebrae, inter-articulating or fused (e.g. following surgery).

Figure 10:
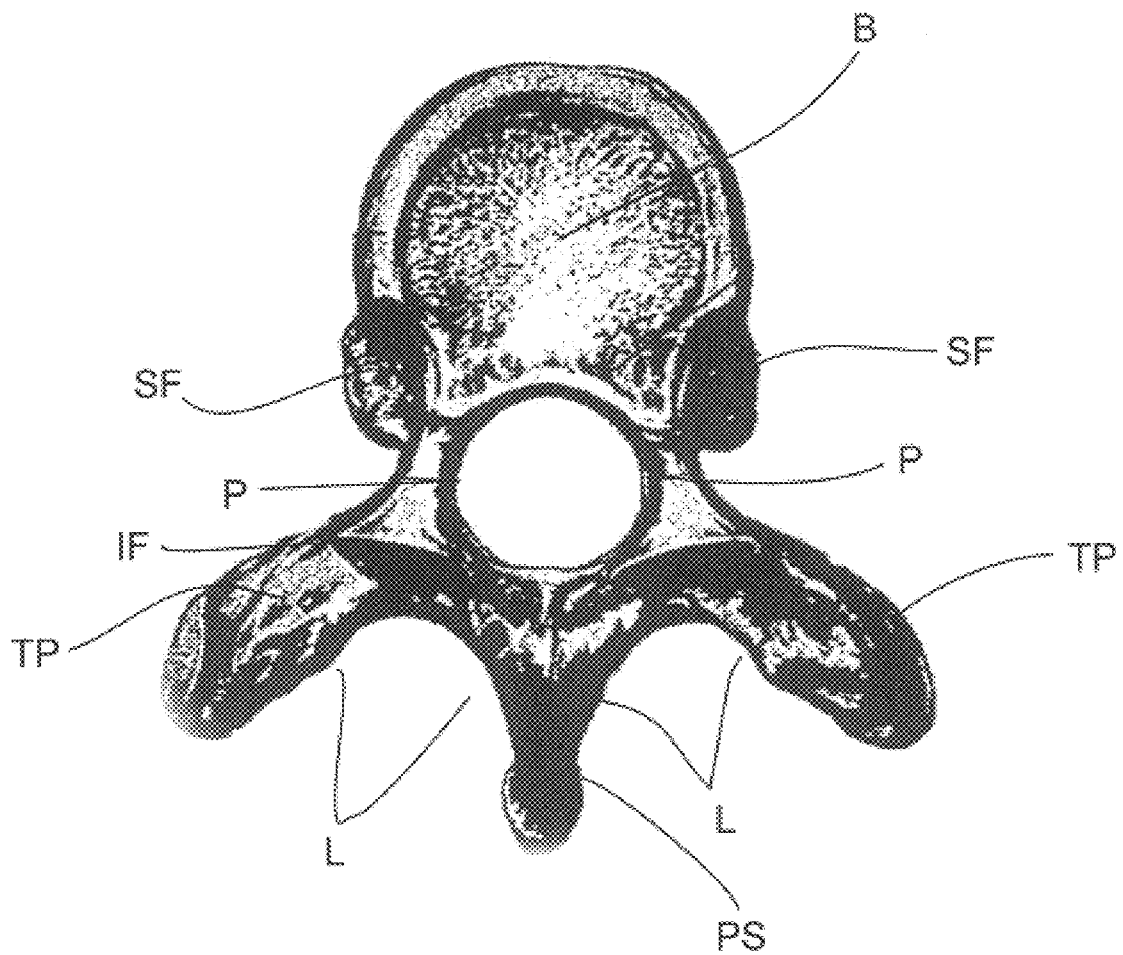
FIG. 10 depicts a human vertebra illustrating the vertebra body (B), the two pedicles (P), the two laminae (L), the transverse and posterior (spinous) processes (PS). and the superior (SF) and inferior facets (IF)
Figure 11:
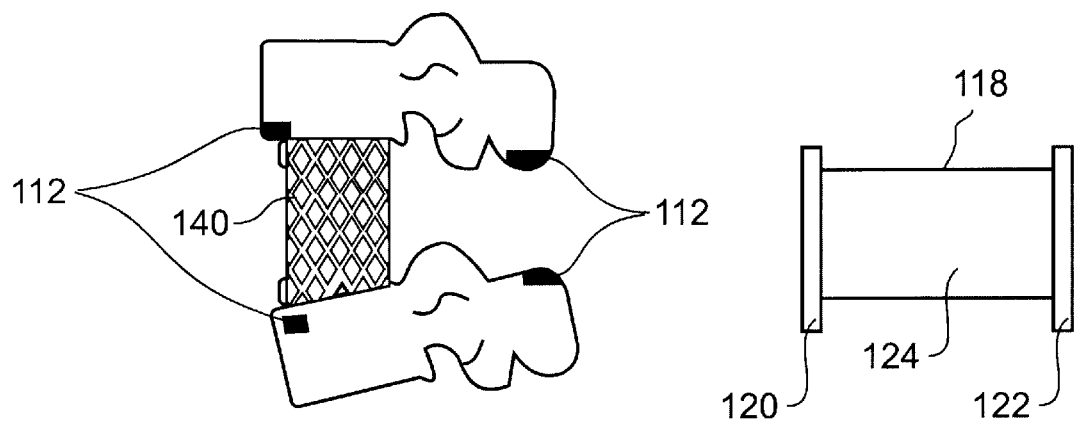
FIG. 11 is a schematic depiction of a detection system for monitoring displacement in vertebrae according to the teachings of the present invention; and FIG, 12 is a schematic depiction of detection system for monitoring displacement between a dental implant and a bone in which it is anchored according to the teachings of the present invention.

FIG. 10 illustrates a human vertebra which is composed of a body (B), two pedicles (P). two laminae (L), transverse and posterior (spinous) processes (PS), and superior (SF) and inferior facets (IF).

FIG. 31, illustrates an implant 140 such as, for example, an internal fixation cage which is used for fixating vertebrae and which includes detection system 112 incorporated therein or attached thereto. In such a case, implant 140 can be fabricated in part from a metallic material which can function as the magnetic element of detection system 112. Detection system 112 can alternatively be implanted within natural vertebrae and/or incorporated into artificial vertebra.

In any case, detection system 112 serves for generating a signal which can be received and processed by extracorporeal unit 118 as described hereinabove, thus enabling to determine a distance between vertebrae.

It will be appreciated that periodical interrogation of detection system 112 following vertebral surgery can provide a physician with information as to the displacement between vertebrae, a parameter which can be utilized to determine the success of a surgical procedure, the general state of an implant or fixated vertebrae and the like.

Detection system 112 and extracorporeal unit 118 of the present invention can be designed and configured for monitoring displacement between a dental implant and the bone into which it was implanted.

Figure 12:
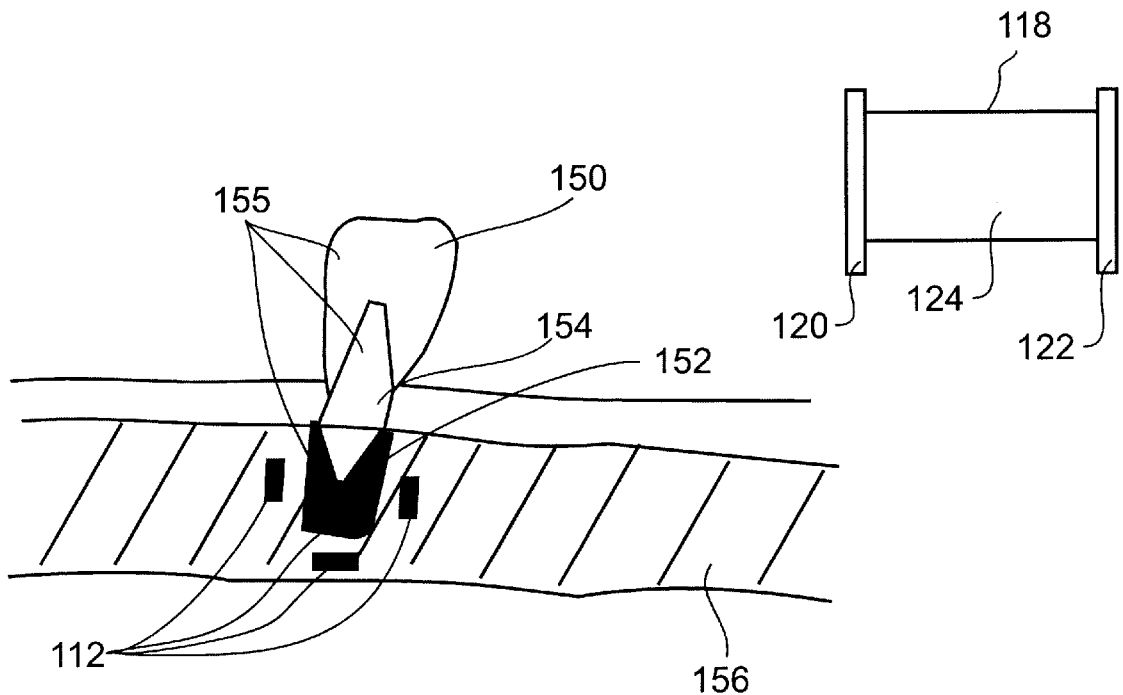

For example, as is specifically shown in FIG. 12, detection system 112 can be utilized to assess the relative displacement between a crown 150, a bone implanted fixture 152 or post 154 of an oral implant 155 and bone 156.

It will be appreciated in this case, that fixture 152 and/or post 154 can be fabricated from a material which in itself can function as the paramagnetic or ferromagnetic element of detection system 112. Alternatively, the paramagnetic or ferromagnetic element can form a part of, or be implanted within, crown 150.

Extracorporeal interrogation of detection system 118 can provide a dental surgeon with information as to the state of the implant and the bone in which it is implanted, thus enabling to detect implant loosening prior to the stage of bone deterioration.

Detection system 112 and extracorporeal unit 118 of the present invention can be designed and configured to monitor displacement between segments of a bone fractured due to a trauma or osteotomy.

Figure 13:
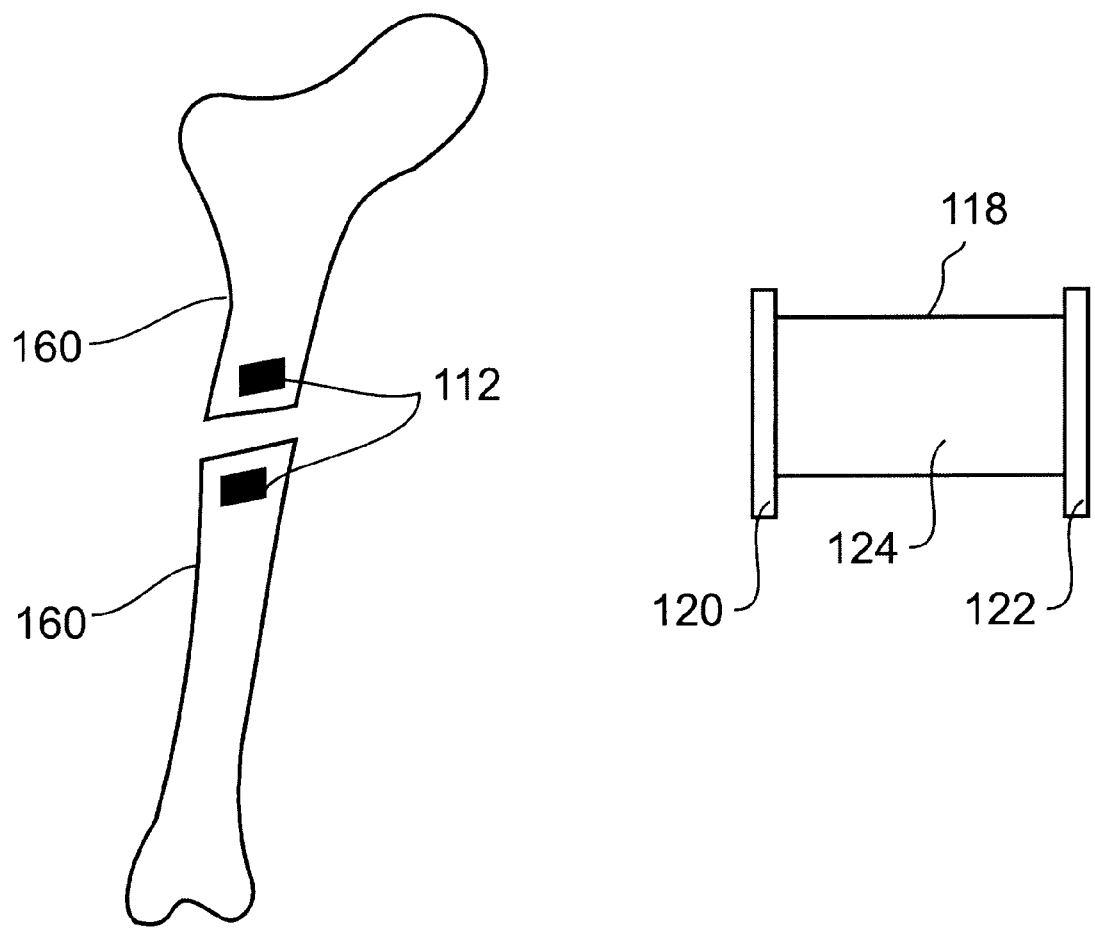
FIG. 13 is a schematic depiction of detection system for monitoring displacement between segments of a fractured bone according to the teachings of the present invention.

As is specifically shown in FIG. 13, detection system 112 can be implanted into two or more bone segments 160 either directly or as a part of a fixating device such as a pin or screw.

Extracorporeal interrogation of detection system 112 via extracorporeal unit 118 as described hereinabove can provide a physician with information relating to the healing state of the fractured or broken bone.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will further be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

What is claimed is:

1. A distance measurement system for monitoring displacements over a joint between two substantially electrically isolated members, the system comprising at a first one of said members at least one resonant circuit;

at a second one of said members at least one magnetic element having predetermined magnetic properties;

and externally to said members:

(c) a transmitter operable to transmit an electromagnetic pulse;

(d) a receiver operable to detect oscillations emitted by said resonant circuit in response to said electromagnetic pulse; and (e) an analyzer operable to analyze an amplitude envelope property of said oscillations, to thereby determine a distance between said resonant circuit and said magnetic element, therefrom to determine a state of said elements at said joint.

2. The distance measurement system of claim 1, wherein said magnetic element is a ferromagnetic element.

3. The distance measurement system of claim 1, wherein said magnetic element is a paramagnetic element.

4. The distance measurement system of claim 1, wherein said analyzer is operable to determine said amplitude envelope property from an absolute value of amplitudes of said oscillations.

5. The distance measurement system of claim 1, wherein said analyzer is operable to determine said amplitude envelope property from relative amplitude values of more than one cycle of said oscillations.

6. The distance measurement system of claim 1, wherein said amplitude envelope property is an amplitude rate of decay.

7. The distance measurement system of claim 1, wherein said analyzer is operable to determine the distance between said resonant circuit and said magnetic element additionally from frequency properties of said oscillations.

8. The distance measurement system of claim 1 comprising more than one resonant circuit, to thereby determine more than one distance between said resonant circuits and said at least one magnetic element.

9. The distance measurement system of claim 8, operable to determine the distance between said resonant circuits and said at least one magnetic element in more than one dimension.

10. The distance measurement system of claim 8, wherein said more than one resonant circuits are operable to resonate at different frequencies.

11. The distance measurement system of claim 1, comprising more than one magnetic element, to thereby determine more than one distance between said at least one resonant circuit and said magnetic elements.

12. The distance measurement system of claim 11, operable to determine the distance between said at least one resonant circuit and said magnetic elements in more than one dimension.

13. The distance measurement system of claim 1, comprising more than one resonant circuit and more than one magnetic element, to thereby determine more than one distance between said resonant circuits and said magnetic elements.

14. The distance measurement system of claim 13, operable to determine the distance between said resonant circuits and said at least one magnetic element in more than one dimension.

15. The distance measurement system of claim 1, wherein said analyzer comprises a look-tip table, comprising relationships between measured oscillations and distances.

16. The distance measurement system of claim 15, wherein said relationships are per-system relationships.

17. The distance measurement system of claim 15, wherein said relationships comprise in-situ calibrations.

18. A method for assembling a distance measurement system to measure displacement between substantially electrically isolated first and second elements over a joint, the method comprising:

(a) placing a resonant circuit at a first location on said first element;

(b) placing a magnetic element with predetermined magnetic properties at a second location on said second element;

(c) providing a transmitter for transmitting an electromagnetic pulse to said resonant circuit;

(d) providing a detector for detecting oscillations emitted by said resonant circuit in response to said electromagnetic pulse; and (e) providing an analyzer in association with said detector for analyzing an amplitude envelope property of said detected oscillations, to thereby determine a distance between said first location and said second location, therefrom to determine a state of said elements at said joint.

19. The method of claim 18, wherein said analyzer comprises a look-up, table of relationships between measured oscillations and distances, and wherein said look-up table values are established for each one of a predetermined set of distances by performing for each predetermined distance the steps of:

(i) transmitting an electromagnetic pulse to said resonant circuit;

(ii) detecting oscillations emitted by said resonant circuit in response to said electromagnetic pulse; and (iii) measuring an amplitude envelope property of said detected oscillations, to thereby establish a look-up table value for said distance.

20. A method for measuring the distance between a first location on a first element, said first location comprising a resonant circuit, and a second location on a second element, said second location comprising a magnetic element, said first and said second elements meeting at a joint, the method comprising the steps of:

(a) transmitting an electromagnetic pulse to said resonant circuit;

(b) detecting oscillations emitted by said resonant circuit in response to said electromagnetic pulse; and (c) analyzing an amplitude envelope property of said detected oscillations, to thereby determine a distance between said first location and said second location, therefrom to determine a state of said elements at said joint.

21. The method of claim 20, wherein the step of analyzing an amplitude envelope property further comprises comparing information detected from said emitted oscillations to information in a look-up table, of relationships between measured oscillations and distances.

22. The method of claim 20, comprising obtaining said amplitude envelope property from an absolute values of amplitudes of said oscillations.

23. The method of claim 20, comprising obtaining said amplitude envelope property from relative amplitude values of more than one cycle of said oscillations.

24. The method of claim 20, comprising making use of an amplitude rate of decay as said amplitude envelope property.

25. The method of claim 20, comprising additionally detecting the distance from frequency properties of said detected oscillations.

26. The method of claim 20, wherein said first element is an artificial joint member and said second element is a natural bone of a joint to which it is attached.

27. The method of claim 20, wherein said first element is a first articulating surface and said second element is a second artificial joint assembly member having a second articulating surface, said first and said second articulating surfaces being in articulating engagement therebetween to form an artificial joint assembly.

28. The method according to claim 20, wherein said first and second elements are respectively vertebrae.

29. The method of claim 20, wherein said first element is a dental implant and said second element is a bone in which said dental implant is anchored.

30. The method of claim 20, wherein said first and said second elements are respectively bone segments of a fractured or broken bone.

31. A distance measurement system for measuring changes in displacement between a first element and a second element meeting at a joint, utilizing eddy currents for energy dissipation, the system comprising:

(a) at least one resonant circuit located within said first element; and (b) at least one magnetic element with predetermined magnetic properties located within said second element;

(c) a transmitter operable to transmit an electromagnetic pulse;

(d) a receiver operable to detect oscillations emitted by said resonant circuit in response to said electromagnetic pulse; and (e) an analyzer operable to analyze an amplitude envelope property of said oscillations as an indicator of eddy current induced energy dissipation, to thereby determine a distance between said resonant circuit and said magnetic element, and therefrom to determine a state of said elements at said joint.

32. A distance measuring system according to claim 31, wherein said first element is an artificial joint member having an articulating surface and a bone attachment portion, said bone attachment portion being for attaching said artificial joint member, to said second element, said second element being a natural bone of a joint when implanted within an individual.

33. The system of claim 31, wherein said first element is a first articulating surface and a said second element is a second artificial joint assembly member having a second articulating surface, said first and said second articulating surfaces being in articulating engagement therebetween to form an artificial joint assembly.

34. The system of claim 31, wherein said first element and said second element are respectively adjacent vertebrae.

35. The system of claim 31, wherein said first element is a dental implant and said second element is a bone in which said dental implant is anchored.

36. The system of claim 31, wherein said first and second elements are respectively bone segments of a fractured or a broken bone.

37. The distance measuring system of claim 32, wherein said at least one artificial joint member includes at least two artificial joint members, each attached to a specific natural bone of said joint of said at least one natural bone of said joint, whereas said articulating surfaces of said at least two artificial joint members are configured to allow articulating engagement therebetween.

38. The distance measuring system of claim 32, wherein said at least one resonance circuit element includes a plurality of distinct resonance circuit elements each producing a distinct signal of oscillating frequency upon reception of said electromagnetic pulse, said distinct signal being a function of a distance between a specific resonance circuit element of said plurality of distinct resonance circuit elements and said at least one magnetic element.

39. The distance measuring system of claim 32, wherein least one artificial joint member forms a part of an artificial joint selected from the group consisting of an artificial shoulder joint, an artificial hip joint, an artificial knee joint, an artificial elbow joint, an artificial ankle joint, an artificial wrist joint, an artificial carpo-metacarpal joint, an artificial metacarpo-phalangeal joint, an artificial interphalangeal joint and an artificial metatarso-phalangeal joint.

40. The distance measuring system of claim 32, wherein said at least one artificial joint member is fabricated from at least one material selected from the group consisting of stainless steel, titanium alloy, cobalt alloy, a polymer, ceramics and composites materials.

41. The distance measuring system of claim 32, wherein said at least one resonance circuit element is implanted within, or attached to, said bone attachment portion of said at least one artificial joint member, and further wherein said at least one magnetic element is implanted within, attached to, or forms a part of said bone attachment portion of said at least one artificial joint member.

42. The system of claim 33, wherein said at least one resonance circuit element includes plurality of distinct resonance circuit elements implanted within or attached to said first artificial joint assembly member, each of said plurality of distinct resonance circuit elements producing a distinct signal of oscillating frequency upon being energized with said electromagnetic pulse, said distinct signal being proportional to a distance between a resonance circuit element of said plurality of distinct resonance circuit elements and said at least one magnetic element.

43. The system of claim 33, wherein said artificial joint assembly is any one of a group comprising an artificial shoulder joint, an artificial hip joint, an artificial elbow joint, an artificial ankle joint, an artificial wrist joint, an artificial carpo-metacarpal joint, an artificial metacarpo-phalangeal joint, an artificial interphalangeal joint and an artificial metatarso-phalangeal joint.

44. The system of claim 33, wherein said artificial joint assembly further includes a third artificial joint assembly member having a third articulating surface, said third articulating surface being in articulating engagement with at least one of said first and said second articulating surfaces.

45. The system of claim 33, wherein said artificial joint assembly is an artificial knee joint.

46. The system of claim 33, wherein said first and said second artificial joint assembly members are each fabricated from at least one material selected from the group consisting of stainless steel, titanium alloy, cobalt alloy, polymer, ceramics and composite materials.

47. The system of claim 33, wherein said first and said second artificial joint assembly members each include a portion distant to said articulating surface thereof, said portion being for attaching each of said first and said second artificial joint assembly members to a natural bone of a joint when implanted within the individual.

48. The system of claim 34, wherein at least one of the vertebrae is an artificial vertebra.

49. The system of claim 36, further comprising at least one anchor element being for attaching said detection system to the bone segments.

50. The system of claim 49, wherein said at least one anchor element forms a part of an implant.

51. The system of claim 50, wherein said implant serves for inter fixating the bone segments.

* * * * *

UNITED STATES PATENT AND TRADEMARK OFFICE
CERTIFICATE OF CORRECTION

PATENT NO. : 6,583,630 B2
DATED : June 24, 2003
INVENTOR(S) : Mendes et al.

It is certified that error appears in the above-identified patent and that said Letters Patent is hereby corrected as shown below:

Column 17,
Line 12, delete the comma "," between the words "look-up" and "table".

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,583,630 B2
DATED : June 24, 2003
INVENTOR(S) : Mendes et al.

It is certified that error appears in the above-identified patent and that said Letters Patent is hereby corrected as shown below:

Title page,
Item [62], Related U.S. Application, please add:
-- This is a Continuation-In-Part of PCT/IL00/00757, filed November 15, 2000
Which takes priority from Serial Number 09/585,318 filed June 2, 2000, now
U.S. Patent No. 6,245,109 and Serial Number 09/443,113, filed November 18, 1999, abandoned. --

Signed and Sealed this

Eighth Day of June, 2004

JON W. DUDAS
*Acting Director of the United States Patent and Trademark Office*